US010481151B2

(12) United States Patent
Passineau et al.

(10) Patent No.: US 10,481,151 B2
(45) Date of Patent: *Nov. 19, 2019

(54) ISOLATION OF PULMONARY ARTERIAL ENDOTHELIAL CELLS FROM PATIENTS WITH PULMONARY VASCULAR DISEASE AND USES THEREOF

(71) Applicant: Allegheny-Singer Research Institute, Pittsburgh, PA (US)

(72) Inventors: Michael J. Passineau, Pittsburgh, PA (US); Srinivas Murali, Pittsburgh, PA (US); Raymond L. Benza, Pittsburgh, PA (US); Jonathan B. Pollett, Pittsburgh, PA (US)

(73) Assignee: Allegheny-Singer Research Institute, Pittsburgh, PA (US)

(*) Notice: Subject to any disclaimer, the term of this patent is extended or adjusted under 35 U.S.C. 154(b) by 122 days.

This patent is subject to a terminal disclaimer.

(21) Appl. No.: 15/806,751

(22) Filed: Nov. 8, 2017

(65) Prior Publication Data

US 2018/0067104 A1 Mar. 8, 2018

Related U.S. Application Data

(63) Continuation of application No. 14/426,488, filed as application No. PCT/US2013/058897 on Sep. 10, 2013, now Pat. No. 9,835,617.
(Continued)

(51) Int. Cl.
*G01N 33/50* (2006.01)
*C12N 5/071* (2010.01)
(Continued)

(52) U.S. Cl.
CPC ......... *G01N 33/5091* (2013.01); *A61B 10/02* (2013.01); *A61M 25/10* (2013.01); *C12N 5/069* (2013.01); *A61M 2202/097* (2013.01); *G01N 2570/00* (2013.01); *G01N 2800/321* (2013.01); *G01N 2800/60* (2013.01)

(58) Field of Classification Search
None
See application file for complete search history.

(56) References Cited

U.S. PATENT DOCUMENTS 9,835,617 B2 * 12/2017 Passineau ............. C12N 5/069

FOREIGN PATENT DOCUMENTS

EP 2372364 5/2011

OTHER PUBLICATIONS

Comhair et al., Am. J. Respir. Cell Mol. Biol. 46(6): 723-730 (2012; available online Mar. 15, 2012).*

(Continued)

Primary Examiner — Erin M. Bowers
(74) Attorney, Agent, or Firm — Fox Rothschild LLP

(57) ABSTRACT

The present disclosure provides methods of obtaining, recovering and culturing pulmonary arterial endothelial cells from an individual patient subjected to a right heart catheterization in regard to diagnosis of pulmonary hypertension. These isolated pulmonary arterial endothelial cells from an individual patient may be utilized to generate cellular phenotyping profile for the cell population, allowing generation of a personalized pharmacotherapy regime to assist the clinician in treatment and prognosis of the disorder for an individual patient.

20 Claims, 2 Drawing Sheets

Related U.S. Application Data

(60) Provisional application No. 61/698,892, filed on Sep. 10, 2012.

(51) Int. Cl.
*A61B 10/02* (2006.01)
*A61M 25/10* (2013.01)

(56) References Cited

OTHER PUBLICATIONS

Taraseviciene-Stewart et al., FASEB J. 15: 427-438 (2001).*
Humbert et al., "Cellular and Molecular Pathobiology of Pulmonary Arterial Hypertension", Journal of the American College of Cardiology, vol. 43, No. 12 Suppl S, Jun. 16, 2004:13S-24S.
Tuder, Rubin M. et al., "Prostacyclin Synthase Expression Is Decreased in Lungs from Patients with Severe Pulmonary Hypertension", American Journal of Respiratory and Critical Care Medicine, vol. 159, No. 6, Jun. 1, 1999, pp. 1925-1932.
Eddahibi, Saadia et al., "Cross Talk Between Endothelial and Smooth Muscle Cells in Pulmonary Hypertension: Critical Role for Serotonin-Induced Smooth Muscle Hyperplasia", Circulation, Lippincott Williams & Wilkins, U.S., vol. 113, No. 15, Apr. 1, 2006, pp. 1857-1864.
Giaid, Adet et al., "Expression of Endothelin-1 in The Lungs of Patents with Pulmonary Hypertension", New England Journal of Medicine, Massachusetts Medical Society, U.S., vol. 328, No. 24, Jun. 17, 1993, pp. 1732-1739.
Sakao, Seiichiro et al., "Endothelial Cells and Pulmonary Arterial Hypertension: Apoptosis, Proliferation, Interaction and Transdifferentiation", Respiratory Research, Biomed Central Ltd., London, GB, vol. 10, No. 1, Oct. 13, 2009.
Pollett, Jonathan B. et al., "Harvest of Pulmonary Artery Endothelial Cells From Patients Undergoing Right Heart Catheterization", Journal of Heart and Lung Transplantation, Mosby-Year Book, Inc., St. Louis, MO, U.S., vol. 32, No. 7, May 15, 2013, pp. 746-749.
Ryan, Una S. et al., "Isolation and Culture of Pulmonary Endothelial Cells", Envrionmental Health Perspectives, vol. 56, Jun. 1, 1984, pp. 103-114.
Abdul-Salam et al., "Proteomic Analysis of Lung Tissues from Patients with Pulmonary Arterial Hypertension", CIRCULATIONAHA. 110.972745, 2010, pp. 2058-2067.
Geraci, Mark W. et al., "Genomics of Pulmonary Arterial Hypertension: Implications for Therapy", Heart Fail Clin. Jan. 2010; 6(1): 101-114.
Dulak, S. B., "A PA Catheter Refresher Course", Modern Medicine, Apr. 2003, http://www.modernmedicine.com/modern-medicine/content/pa-catheter-refresher-course.
Grignola, J. C., "Hemodynamic Assessment of Pulmonary Hypertension", World Journal of Cardiology, Jan. 26, 2011; 3(1): 10-17.
Sprecher, D. L. et al., "Histopathologic Examination of Material from Angioplasty Ballon Catheters Used in Vivo in Human Coronary Arteries", Atherosclerosis, Feb. 1989, vol. 75, Issues 2-3, pp. 237-244.
Duong H. T. et al., "Pulmonary Artery endothelium Resident Endothelial Colony-Forming Cells in Pulmonary Arterial Hypertension", Pulmonary Circulation, vol. 1, No. 4 (Oct. 2011), pp. 475-486.

* cited by examiner

ISOLATION OF PULMONARY ARTERIAL ENDOTHELIAL CELLS FROM PATIENTS WITH PULMONARY VASCULAR DISEASE AND USES THEREOF

RELATED APPLICATIONS AND CLAIM OF PRIORITY

This patent document claims priority to, and is a continuation of, U.S. patent application Ser. No. 14/426,488, filed Mar. 6, 2015 (the "488 application"). The '488 application is a national stage application of, and claims priority to, International Patent Application No. PCT/US2013/058897, filed Sep. 10, 2013, which in turn claims priority to U.S. Provisional Patent Application No. 61/698,892, filed Sep. 10, 2012. The disclosures of each priority application listed above are fully incorporated into this document by reference.

TECHNICAL FIELD

Removal, isolation and in vitro cell culture of pulmonary arterial endothelial cells ("PAECs") from individual living patients showing symptoms of or having been diagnosed with pulmonary vascular disease are disclosed. These patient-derived PAECs will provide previously unavailable diagnostic and prognostic tools for treating pulmonary vascular disease, including but not limited to use in various assays and screens to identify cellular phenotypic characteristics as well as performing full proteonomic protein expression profiles for any recovered and substantially purified PAEC population obtained as disclosed herein, thus supporting future diagnostic and prognostic indications in the form of a personalized pharmacotherapy regime related to progressive pulmonary vascular disease states. Additional uses for these PAECs relate to use in applicable in vitro-based cell assays and screens for the purpose of identifying novel compounds to treat one or multiple forms of pulmonary vascular disease, as well as selecting various PAECs to establish immortalized cell lines to practice other embodiments.

BACKGROUND

Pulmonary hypertension ("PH") is a pathological elevation of blood pressure within the pulmonary circulation which is initiated with inflammation and changes in endothelial cells lining the pulmonary artery. As discussed herein, PH is divided into five groups based on its causes, with each group indication showing mean pressure in the pulmonary arteries of greater than 25 mmHg at rest or 30 mmHg during physical activity, with normal pulmonary artery resting mean pressure being within a range of 8-20 mmHg. A form of PH, pulmonary arterial hypertension ("PAH"), is a chronic, progressive and ultimately fatal disease which includes symptoms such as increased pulmonary vascular resistance of the lung microvasculature, intimal hyperplasia, smooth muscle hypertrophy and in situ thrombosis. Whether caused by a single or via multiple factors, one common thread to PAH is marked PAEC dysfunction, where progression of the disease associates with notable increases in vasoconstrictor and proliferation mediators while showing a concomitant decrease in vasodilator and antiproliferative agents.

Pulmonary arterial hypertension is notoriously difficult to successfully treat, leading, in part, to its poor prognosis. A first line therapy for treating PAH includes ET-1 receptor antagonists ("ERAs"), which either selectively inhibit the $ET_A$ membrane receptor (e.g., sitaxsentan and ambrisentan) localized to pulmonary arterial smooth muscle cells, or antagonists which non-selectively bind both the $ET_A$ and $ET_B$ membrane receptor (e.g., besentan); the $ET_B$ receptor being localized to both pulmonary arterial smooth muscle cells and pulmonary arterial endothelial cells. Another primary therapy includes selective inhibitors of phosphodiesterase-5 (e.g., sildenafil). Antagonists of PDE-5 are thought to prolong NO availability, a potent pulmonary vasodilator. One late stage therapy includes administration of a prostacyclin analogue (including epoprostenol, a synthetic form of the natural prostaglandin derivative $PGI_2$ provided as a sodium salt). Prostacylcin is a potent vasodilator with antiproliferative characteristics that shows marked decrease in patients diagnosed with PAH. Unfortunately, these prostacyclin analogues (also including treprostinil [subcutaneous injection] and iloprost [via inhalation]) possess such a short half life (about 6 minutes) that the drug must be administered intravenously over a prolonged time frame. Although these therapies can be used, great variability exists among patients in their response. This variability includes dramatically greater or lesser response to therapy in individual patients versus the response that is expected based on other prognostic factors. Pulmonary arterial hypertension is further classified into either an "associated" form, where there is an identifiable cause for the pulmonary vascular changes or two related diseases known as idiopathic PAH (IPAH), where no identifiable cause exists, and familial PAH (FPAH), in which the disease is related to mutations in the BMPR2 gene. One of the major challenges in establishing a therapeutic regimen is that different patients respond differently to first-line therapies, specifically ERAs and PDE-5 antagonists, and it is presently impossible to predict which class of drugs will be more effective in a newly diagnosed PAH patient. The present invention addresses these clinical needs through isolation of PAECs from individual patients suffering from pulmonary vascular disease, including PAECs from patients diagnosed with or showing symptoms of PAH, thus allowing for methods utilizing such PAECs to provide diagnostic and prognostic indications for personalized pharmacotherapy to treat progressing pulmonary vascular disease states, as well as using PAECs described herein to screen for drugs useful in the treatment of pulmonary vascular disease, and providing primary and secondary PAECs for generation of phenotype-specific immortalized cell lines.

SUMMARY

This document discloses a method of obtaining PAECs recovered directly from the pulmonary vasculature of living patients via a right heart catheterization procedure indicated for diagnosis of PV disease, such as but not limited to various forms of pulmonary arterial hypertension. A patient total cell population recovered during the procedure is separated away from the spent catheter and subjected to a cell sorting process to substantially purify PAECs cells away from the patient's total cell population. These purified patient PAECs may then be initially amplified in cell culture and utilized in multiple further embodiments, including but not limited to (i) utilizing a patient's recovered, sorted and cultured PAECs in one or multiple in vitro screens or assays to measure the phenotypic characteristics indicative of the stage of PH and/or to measure the cellular response (including but not limited to altered intracellular signaling components related to vasodilator and/or vasoconstrictor agents oftentimes observed within dysfunctional PAECs associated with PH, the agents themselves (including but not limited to endothelin-1, cGMP, phosphodiesterase-5 and prostacyclin); and, (ii) again utilizing a patient's recovered, sorted and cultured PAECs in one or multiple in vitro screens or assays to measure the phenotypic characteristics indicative of detectable transformation of at least a relevant percentage of PAECs from a normalized cellular apoptotic state to a hyper-apoptotic state (potentially indicative of early stage PV disease) or an anti-apoptotic state (potentially indicative of a more advanced stage of PV disease); such a transformation, or degree thereof, thus being indicative of disease progression. The measured phenotypic characteristics of a patient's PAECs of (i) and (ii) herein will allow the clinician to generate or alter a personalized pharmacotherapy regime specifically suited for that individual patient. It will be understood upon review of this document that a particular patient's treatment regime requiring multiple catheterization procedures offers the opportunity to bank a patient's PAECs on multiple occasions. Such a strategy allows for the continued monitoring of key variables disclosed herein, including but not limited to an ability for the clinician to used such an expanded time frame for multiple collection of data as per applications (i) and (ii) above. This compilation of multiple PAECs data sets over the course of the patient's continued treatment will provide the clinician with the ability compare data going forward and, if necessary, allow for alteration in the personal pharmacotherapy regime specifically for that particular patient.

The disclosed embodiments further relate to use of the purified PAECs as disclosed herein for use in applicable in vitro-based cell screens and assays for the purpose of identifying novel compounds which may be useful in treating one or more forms of pulmonary vascular disease, including but not limited to screening drug candidates (such as via one or multiple compound libraries available to the artisan) to identify and select compounds which effect PAEC phenotype, including phenotypic characteristics indicative of the stage of PH and/or to measure the cellular response, including but not limited to altered intracellular signaling components related to vasodilator and/or vasoconstrictor agents oftentimes observed within dysfunctional PAECs associated with PH, and/or the agents themselves (including but not limited to endothelin-1, cGMP, phosphodiesterase-5 and prostacyclin).

The disclosed embodiments also relate to using the purified primary PAECs obtained from a patient to establish secondary cultured cell lines and/or immortalized cell lines from selected procedures for the use in various applications, including cellular phenotyping activities to generate a patient-specific personalized pharmacotherapy regime as disclosed herein, subjecting PAECs obtained from a living patient to full-proteonome profiling, as well as in applicable in vitro-based cell screen and assays for the purpose of screening for and selecting novel compounds which may be useful in treating pulmonary vascular disease.

This document further discloses embodiments relating to the use of purified PAECs obtained from a living patient, by methods as disclosed herein, for use in generating a relevant full-proteonomic profile (also referred to in the art as a "proteonomic profile", "proteonome profile" and/or "full-proteonome profile") or a class of or multiple classes of PAEC-based proteonomic profiles which will allow the clinician to generate or alter a personalized pharmacotherapy regime specifically suited for an individual patient or class of individual patients. Again, such a personalized pharmacotherapy regime may be subject to alteration during the course of treatment. For example, noting that a particular patient may require multiple catheterization procedures over time. This necessity at least offers the clinician an opportunity to bank a patient's PAECs on multiple occasions, allowing for compilation of multiple PAECs data sets over the course of the patient's continued treatment. And in turn, provides an opportunity to review this data in the aggregate, which may result in continuing a current treatment regime or possibly indicating a preference for altering the personal pharmacotherapy regime specifically for that particular patient.

This document further discloses PAECs obtained from individual patients by the methods disclosed herein, including but not limited to PAECs subjected to removal from the individual patient and a relevant cell sorting technique to provide for a substantially pure collection of the patient's PAECs, an isolated PAEC population further provided through known cell subculture techniques, any isolated patient-derived PAEC cell line available in any useful form, such as but not including a cryopreserved PAEC cell line, and a PAEC-derived cell line which is an immortalized or transformed cell line, especially relating to an immortalized or transformed PAEC-derived cell line which exhibits a cellular phenotype of interest as related to generating a personalized pharmacotherapy regime as disclosed herein.

DETAILED DESCRIPTION

Figure 1:
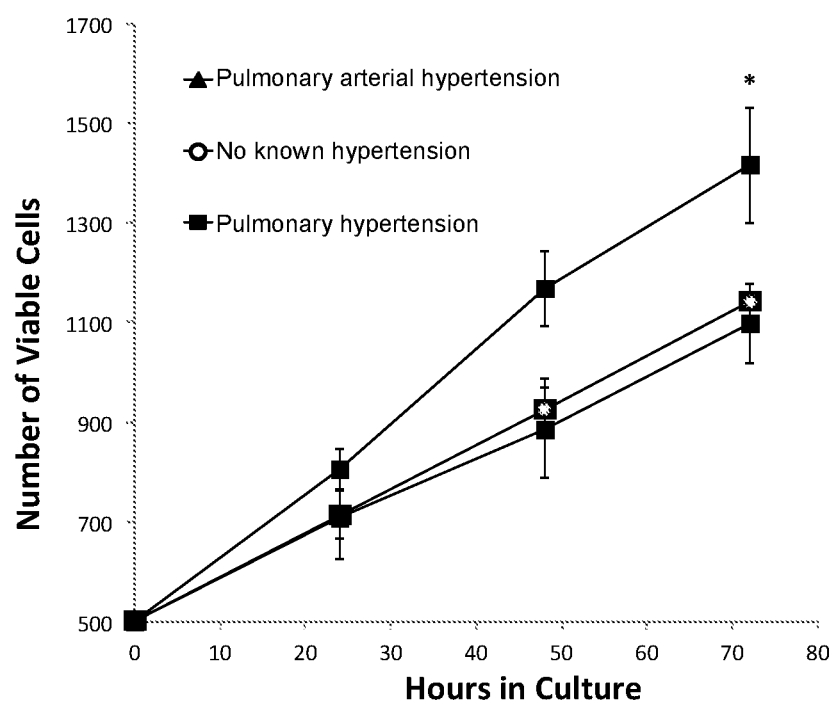
FIG. 1 shows growth kinetics of PAH, PH and control (no known hypertension) PAECs.

Before methods and composition provided herein are described, it is to be understood that this invention is not limited to the particular processes, methodology or composition described, as these may vary. It is also to be understood that the terminology used in the description is for the purpose of describing some embodiments, and is not intended to limit the scope of the present invention. All publications mentioned herein are incorporated by reference in their entirety to the extent to support the present invention.

It must be noted that, as used herein and in the appended claims, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present invention.

The terms "improve" or "improves" is used to convey that a therapeutic or the application of a method disclosed herein changes either the appearance, form, characteristics and/or physical attributes of the subject to which it is being provided, applied or administered. "Improve" or "Improves" may also refer to the overall physical state of an individual to whom an active agent has been administered. For example, the overall physical state of an individual may "improve" if one or more symptoms of a disorder or disease are alleviated by administration of an active agent or by selecting an agent based upon a personalized pharmacotherapy regime.

As used herein, the term "therapeutic" or "therapeutic agent" means an agent utilized to treat, combat, ameliorate or prevent an unwanted condition or disease of a patient, with symptoms of or having been previously diagnosed with pulmonary vascular disease, including but not limited to PH, and as such, pulmonary arterial hypertension. In some embodiments, a therapeutic or therapeutic agent may be a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The terms "treat," "treated," or "treating" as used herein refers to both therapeutic treatment and prophylactic or preventative measures, wherein the object is to prevent or slow (lessen) an undesired physiological condition, disorder or disease, or to obtain beneficial or desired clinical results. For the purposes of this invention, beneficial or desired clinical results include, but are not limited to, alleviation of symptoms, diminishment of the extent of the condition, disorder or disease, stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. The disorder, for example, can in general be PH, and more specifically, PAH.

Some embodiments relate to identifying phenotypic characteristics of a patient's PAECs to serve as a comparator in treating various PH disorders. The term "personalized pharmacotherapy" or "personalized pharmacotherapy regime" refers to the ability of the clinician to provide a cellular phenotypic work-up of the patient's PAECs, a work-up which will allow the clinician to tailor a patient-specific "personalized pharmacotherapy regime" (i.e., "personalized pharmacotherapy") to indicate an initial diagnostic strategy as well as providing relevant prognostic indicators; such a work-up made possible as per various disclosed embodiments of the present invention. The clinician may use this analysis to generate an initial or alternative therapeutic strategy as a path forward for treating the individual patient (hence, the terms "personalized pharmacotherapy" and "personalized pharmacotherapy regime"). Such a strategy may be based solely on the results of the cellular phenotypic analysis from that specific patient's PAECs, whether obtained through a one time catheterization procedure or via multiple catheterization procedures for that individual patient. Alternatively, such a strategy may be formed through comparing the phenotypic profile from the individual's PAECs to phenotypic profiles generated previously from different patients who received a course of therapy shown to exert an effect (positive, negative or neutral as related to each measured phenotype) in treating that specific PV-based disorder in response to a particular therapeutic regime. Also, such a strategy may be formed through proteonomic profiling of PAECs derived from one or multiple living patients subjected to a diagnostic right heart catheterization procedure, as disclosed herein. As an example, but not to suggest a limitation, personalized pharmacotherapy may also apply when a patient's PAECs are subjected to phenotypic analysis to determine the absence or presence (or degree) of either a hyper-apoptotic state or an anti-apoptotic phenotype. Data generated from any such screen or assay will provide the clinician an additional disease state indicator allowing for diagnostic and prognostic indications for treating the respective form of PH. Such a personalized pharmacotherapy regime may be subject to alteration during the course of treatment. For example, a particular patient may require multiple catheterization procedures over time. This necessity at least offers the clinician an opportunity to bank a patient's PAECs on multiple occasions, allowing for compilation of multiple PAECs data sets over the course of the patient's continued treatment. And in turn, providing an opportunity to review this data in the aggregate, which may result in continuing a current treatment regime or possibly indicating a preference for altering the personal pharmacotherapy regime specific to that particular patient.

The term "patient" generally refers to any living organism to which a compound is administered to or from which a sample is taken to perform a method described herein. A patient can be an animal, such as a human. A patient may also be domesticated animal or a farm animal. A patient may also be referred to as a subject.

The term "compound" refers to inorganic or organic chemical or biological compounds either natural (isolated) or synthetic, and especially encompass nucleic acids, proteins, polypeptides, peptides, glycopeptides, lipids, lipoproteins and carbohydrates.

It will be understood that the term "pulmonary vascular disease" denotes a category of disorders which all affect the blood circulation in the lungs. As used herein, "pulmonary hypertension" in general, and "pulmonary arterial hypertension" specifically, is defined as an elevation in mean pulmonary arterial pressure to >25 mmHg at rest or 30 mmHg during exercise. It is a hemodynamic abnormality, which is common to a variety of diseases and syndromes. Elevation in pulmonary arterial pressure causes an increase in right ventricular (RV) afterload, impairing RV function and ultimately leading to RV failure and death. Specific histopathologic features, regardless of cause, characterize PAH. Examples of these common features include, but are not limited to, medial hypertrophy, intimal proliferation, concentric laminar fibrosis, and plexiform and thrombotic lesions. Endothelial cell injury may lead to each of these patterns via the elaboration of endothelium-derived mediators, which favor smooth muscle cell proliferation, hypertrophy, and inhibition of apoptosis leading to vasoconstriction, neointimal formation medial hypertrophy, and thrombosis. Use of the term "pulmonary hypertension" (or "PH") is meant to encompass and include all forms of PH, including (i) pulmonary arterial hypertension, (ii) pulmonary hypertension with left heart disease, (iii) pulmonary hypertension associated with lung diseases and/or hypoxemia, (iv) pulmonary hypertension due to chronic thrombotic and/or embolic disease, and (v) other miscellaneous culprits, including but not limited to sarcoidosis, histiocytosis X, lymphangiomatosis, and compression of pulmonary vessels (e.g., adenopathy, tumor, fibrosing mediastinitis).

As discussed herein, the disclosed embodiments provide methods of tailoring a patient's treatment based on generation of a personalized pharmacotherapy regime. The therapy can be an FDA approved therapy or an experimental therapy. For example, the therapy may be an ET-1 receptor antagonist (ERAs), which either selectively inhibits the $ET_A$ membrane receptor (sitaxsentan and ambrisentan) or which non-selectively binds both the $ET_A$ and $ET_B$ membrane receptor (besentan). Another primary therapy includes selective phosphodiesterase-5 antagonists (sildenafil). Also available are calcium blockers (amlodipine, diltiazem and nifedipine) and prostacyclin analogues (epoprostenol, treprostinil, and iloprost). In certain embodiments, ERAs are utilized for treatment of PAH in patients that have been identified as having an improved response to a PAH treatment.

In some embodiments, the response to the treatment that is predicted is an increase or prolonging of survival of the patient. In some embodiments, the prediction is an increase in the distance walked in the six-minute walk distance test, which may be referred to as 6MWD. Accordingly, in some embodiments, the response that is predicted through generation of a personalized pharmacotherapy regime is an increase in the distance walked in the 6MWD test. In some embodiments, the personalized pharmacotherapy regime predicts an increase in quality of life in the patient. Although an increase in quality of life can be somewhat subjective, in some embodiments, an increase in quality of life correlates to an increase in the distance during the 6MWD test.

In some embodiments, the personalized pharmacotherapy regime predicts an improvement in hemodynamic parameters, such as but not limited to, right atrialiventrical pressure, cardiac index, pulmonary vascular resistance, and the like. Accordingly, in some embodiments, one or more hemodyamic parameters is predicted to be improved in response to a treatment based upon a change in treatment in response to phenotypic read-out from in vitro cell-based screens or assays, or via singular or multiple PAEC-based proteonomic profiling from one or multiple living patients which may dictate a personalized pharmacotherapy regime which follows a different therapeutic regime as a path forward in treating an individual disease state, including but not limited to drug selection, identification of optimal dosing, maximizing drug efficacy and/or minimizing the risk of toxicity. In some embodiments, one or more hemodyamic parameters is predicted not to be improved in response to a treatment in response to phenotypic read-out from the in vitro cell-based screens or assays, or alternatively, in response to a singular or multiple patient PAEC-based proteonomic profile. Additionally, as similarly noted in this paragraph, in some embodiments, the methods can be used to predict an improvement in a patient's echocardiogram and/or BNP (brain natriuretic peptide) and/or a functional class. And to this end, in some embodiments, the disclosed methods provide for an improvement in one or more or any combination of the clinical endpoints described herein. In some embodiments, the methods predict that there will not be an improvement in one or more or any combination of the clinical endpoints described herein.

In addition to the clinical outcomes described herein, in some embodiments, the therapeutic efficacy predicted may be improving drug selection (e.g., identifying the most effective drug/therapeutic for the patient), identifying optimal dosing, maximizing drug efficacy and/or minimizing the risk of toxicity. In certain embodiments the therapeutic efficacy predicted may be overall outcome (e.g., morbidity and/or mortality) for said patient. In certain embodiments, the therapeutic efficacy predicted through the personalized pharmacotherapy regime may be whether said patient will be more likely or less likely to respond to a particular drug, e.g., ERAs. In certain embodiments, the therapeutic efficacy predicted may be whether proposed drug therapy, e.g., ERAs, will be effective in treating PH disorders, including but not limited to PAH. For example, in certain embodiments, the method of screening may be indicative of whether the patient will have improved walking, such as long-term 6MWD, when treated with a therapeutic, including for example, ERAs. In certain embodiments, the method of screening may be indicative of whether the patient will have improved long-term and/or short-term functional capacity, as measured for patients with PAH.

In some embodiments, the present invention provides methods of predicting a time to clinical worsening endpoint in a patient with pulmonary hypertension comprising screening said patient's PAECs to generate phenotypic read-out from in vitro cell-based screens or assays or a proteonomic profile to predict such a time to a clinical worsening endpoint, where for example an in vitro cell-based screen or assay measures a high percentage of a hyper-apoptotic and/or anti-apoptotic endothelial cells within the patient's PAEC sample.

In additional embodiments of this disclosure methods are provided to generate personalized pharmacological profiles or treatment regimes for a living patient showing symptoms of or having been previously diagnosed with some form of PV disease, such as PH (and including but not limited to PAH) based on proteonomic profiles generated from at least substantially purified PAECs derived either from a single patient and/or multiple sources of PAECs from multiple patients having been subjected to a right hearth catheterization procedure, for whatever the reason. Thus, the disclosure herein of obtaining, sorting and culturing PAECs from living PV patients allows for large scale analysis of endothelial cell phenotyping. And in this particular embodiment relating to generation of a proteonomic profile for multiple PAEC samples, allowing for identification of relevant protein expression profiles from, say, 'classes' of PAEC, thus providing the clinician additional information to allow for generating a personalized pharmacologic regime for a specific PV patient based on their individual PAEC-based proteonomic profile. A statistically relevant number of PAEC samples obtained from classes of patients would be subjected to proteonomic profiling based on one or several class factors, including but not limited to the stage of PV disease, the drug therapy (either as a single drug or a combination therapy) a class of patients has been receiving over a period of time, and especially a combination of these two classes or indications. Thus, results from such protein expression profiling may reveal cellular phenotypic patterns reflective of the disease stage, the current drug therapy treatment regime, and/or the prognostic state of patients within a certain class which reveal a specific or pattern-related full-proteonomic profile. As an example, but not intended as a limitation, comparison of full proteonomic profiles from a class of patients receiving an ERA to treat, for example, PAH, may reveal a distinctive protein expression profile which may indicate continued treatment with the same ERA, or possibly switching the drug therapy regime to a different ERA, a different class of drugs for treating the specific form of PV, or possibly consideration of a combination therapy. The continual banking of such PAECs-derived proteomic profile data (whether representing either a partial or complete proteomic profile) representing patients at different disease stages which have responded positively, negatively, or neutrally to one or more different drug treatment regimes will provide data which will assist the clinician in formulating a personalized pharmacological regime for a PAECs patient based on results obtained from a proteonomic profile of PAECs obtained from an individual living patient. Additionally, proteomic profiling from multiple PAEC samples will identify up- or down-regulated endothelial cell proteins (as compared to controls such as other obtained PAECs or endothelial cells representative of a healthy individual) within these dysfunctional PAECs, which by their altered expression pattern may represent a useful PV-related biomarker to assist the clinician in formulating a personalized pharmacological regime, or as a biomarker or actual target protein to in support of drug screening methodology available in the art to screen and select for compounds which may be useful as a drug therapy to treat PV.

To this end, various embodiments relate to a method of obtaining PAECs recovered directly from the pulmonary vasculature of living patients via a right heart catheterization procedure indicated for diagnostic confirmation of pulmonary vascular disease, such as PH, and especially PAH. A patient total cell population recovered during the procedure is separated away from the spent catheter and subjected to a cell sorting process to substantially purify PAECs away from the patient's total cell population. These purified patient PAECs may then be initially amplified in cell culture and utilized in multiple further embodiments of the present invention, including but not limited to (i) utilizing a patient's recovered, sorted and cultured PAECs in one or multiple in vitro screens or assays to measure the phenotypic characteristics indicative of the stage of PH and/or to measure the cellular response (including but not limited to altered intracellular signaling components related to vasodilator and/or vasoconstrictor agents often times observed within dysfunctional PAECs associated with PH, the agents themselves (including but not limited to endothelin-1, cGMP, phosphodiesterase-5 and prostacyclin); and (ii) utilizing a patient's recovered, sorted and cultured PAECs in one or multiple in vitro screens or assays to measure the phenotypic characteristics indicative of detectable transformation of at least a relevant percentage of PAECs from a normalized cellular apoptotic state to a hyper-apoptotic state or an anti-apoptotic state, such a transformation (or degree thereof) being indicative of disease progression, with a hyper-apoptotic phenotypic tendency suggesting an earlier stage of the PV disease and an anti-apoptotic state suggesting a later stage of the PV disease. The measured phenotypic characteristics of a patients PAECs of (i) and (ii) herein will allow the clinician to generate a personalized pharmacotherapy regime specifically suited for that individual patient which may involve a strategy to either initially select a drug of choice for patient administration or, in the alternative, to modify the present drug treatment regime based on the read-out of the cellular phenotypic profile. The results from such assays or screens may suggest selection of a drug from a certain class of therapeutic agents; a specific drug in any such class of therapeutic agents; a single, stand-alone therapy option; or possibly may point to a combination therapy (within or among therapeutic classes) as the most prudent treatment strategy providing the optimal prognosis. To this end, the disclosed embodiments relate to methods of obtaining PAECs directly from the pulmonary vasculature of living patients which comprises retrieving these cells from the individual patient, substantially purifying the PAECs away from the total cell population, amplifying the PAECs in cell culture and utilizing these substantially purified PAECs (whether as primary in vitro cultured cells, secondary in vitro cultured cells, or as an immortalized cell line) in one or multiple in vitro cell-based assays or screens or a PAEC-based phenotype profile enabling the clinician to generate and provide a patient-specific personalized pharmacotherapy regime concerning the treatment of the specific PH disorder. Thus, such a personalized pharmacotherapy regime may also be enhanced through comparison of the current patient's cellular phenotypic profile or proteonomic profile to other cellular phenotypic profiles or proteonomic profiles generated from isolated PAECs derived from previously monitored patients. Observed similarities (or differences) and/or patterns when comparing profiles may point the clinician to or away from the course of treatment given to such an individual patient, based on the earlier recorded outcome. The disclosed embodiments further relate to use of the purified PAECs as disclosed herein for use in applicable in vitro-based cell screens and assays for the purpose of identifying novel compounds which may be useful in treating one or more forms of pulmonary vascular disease. The disclosed embodiments also relate to using the purified primary PAECs obtained from a patient to establish immortalized/transformed cell lines from selected procedures for the use in various application, including cellular phenotyping activities (such as for proteonomic profiles) and in applicable in vitro-based cell screen and assays for the purpose of identifying novel compounds which may be useful in treating pulmonary vascular disease. It will be understood upon review of this document that a particular patient's treatment regime requiring multiple catheterization procedures offers the opportunity to bank a patient's PAECs on multiple occasions. Such a strategy allows for the continued monitoring of key variables disclosed herein, including but not limited to an ability for the clinician to used such an expanded time frame for multiple collection of data as per applications (i) and (ii) above. This compilation of multiple PAECs data sets over the course of the patient's continued treatment will provide the clinician with the ability compare data going forward and, if necessary, allow for alteration in the personal pharmacotherapy regime specifically for that particular patient. Of course, any such personalized pharmacotherapy scheme may be generated from multiple profiles where each of the proteomic profiles (either a partial or complete proteomic profile) represents a sample obtained from the a specific, individual patient; or possibly represent a series of such profiles generated from any combination of data sets, including but not limited to being one or more profiles generated during the course of treatment from a sole individual patient in combination with one or more profiles generated from unrelated, separate patients. Obviously, any combination of profiles generated from patient PAECs and profiles generated from 'unrelated' PAECs, as noted herein, will be useful in generating and/or updating the individual's personal pharmacotherapy regime; profiles which may be chosen for comparison based on similar, somewhat similar, or possibly different profiles as those of the patient, possibly based on the current and proposed treatment regime for that individual patient moving forward.

Major types of pulmonary vascular disease include, but are not limited to pulmonary embolism, chronic thromboembolic disease, pulmonary veno-occlusive disease, arteriovenous malformations and pulmonary edema. Pulmonary hypertension (PH) represents a broad term covering various pulmonary vascular disease states, which include (i) pulmonary arterial hypertension, (ii) pulmonary hypertension with left heart disease, (iii) pulmonary hypertension associated with lung diseases and/or hypoxia, (iv) pulmonary hypertension due to chronic thrombotic and/or embolic disease, and (v) other miscellaneous culprits (see Simonneau et al., 2004, J. Amer. Coll. Cardiol. 43 Suppl 1 (12):S5-S12). As noted, another form of PH is pulmonary arterial hypertension (PAH) which includes pulmonary veno-occlusive disease and pulmonary capillary hemangiomatosis, as well as idiopathic PAH (IPAH), familiar PAH (FPAH) and associated PAH (APAH). One particular embodiment of the present invention relates to a method of obtaining pulmonary vascular cells directly from the pulmonary vasculature of a living patient diagnosed with or showing symptoms of PAH, and especially a population of PAECs from a patient diagnosed with or showing symptoms of PAH. Once the total cell population has been removed from the PAH patient, this total cell population is subjected to a cell sorting process to substantially purify PAECs away from the total cell population. These purified primary PAECs obtained from the individual PAH patient supply a source of cells for direct utilization in the practice of additional embodiments of the present invention as disclosed herein, including but not limited to using the PAECs to generate a personalized pharmacotherapy regime assisting the clinician is determining whether the current course of action between available drug therapies represents a best path forward in treating the disease, or whether a different drug or combination thereof is warranted based on phenotypic and/or genotypic characteristics of the patient's PAECs; the additional use of the primary PAECs in measuring the any hyper-apoptotic and/or anti-apoptotic phenotype of the patient's recovered PAECs, which will provide the physician with additional information for future pharmacologic intervention, including but not limited to a clinical decision-making point for initiating or continuing prolonged administration of a prostacyclin analogue (including but not limited to epoprostenol, a synthetic form of the natural prostaglandin derivative $PGI_2$ provided as a sodium salt), which has historically shown to be effective in treating PAH, but possesses such a short half life (about 6 minutes) that the drug must be administered intravenously over a prolonged time frame; additionally the use of these purified primary PAECs obtained from the PAH patient to use directly in applicable in vitro-based cell screens and/or in vitro-based cell assays for the purpose of identifying novel compounds which may be useful in treating pulmonary vascular disease (and especially PAH); and additionally using the purified primary PAECs obtained from the PAH patient to establish immortalized lines from selected patient procedures for the use in applications such as applicable in vitro-based cell screen and assays for the purpose of identifying novel compounds which may be useful in treating PH (and especially PAH). As noted above, PH, which includes PAH as a subcategory, is a pathological elevation of blood pressure within the pulmonary circulation. The management of patients with PH involves initial detection of the presence of PH, a confirmation of the presence of PH and finally, establishing a clinical path forward for treating the disease (such as PAH) based on the present severity of the disease, the associated or causal conditions of the disease, as well as the functional status of the patient and the overall prognosis (see McLaughlin and McGoon, 2006, Circulation 114 (13): 1417-1431). Diagnostic strategies with PH (and as such, PAH) may include initially performing an echocardiogram, followed by chest X-ray, sleep studies, a ventilation-perfusion scan, autoantibody tests, and/or an HIV test. While results from these clinical tests may lead to a specific diagnosis of PAH, the definitive test to establish a diagnosis remains right heart catheterization, where a catheter is introduced into an appropriate central, peripheral or radial vein, advanced through the right heart and ultimately wedged in a branch of the pulmonary artery in order to obtain a pressure reading. Standard practice has been to discard the catheter. The present invention discloses a stark departure from this accepted procedure. Instead of discarding the catheter altogether, the spent catheter (subsequent to removal from the patient) is washed to remove any cells which remain adhered to the catheter subsequent to removal from the patient. These cells ("a total cell population") from the patient are collected and sorted to substantially isolate the patient's PAECs away from the total cell population. The patient's PAECs may then be subjected to conventional cell culture techniques, including known methods to proliferate the cells in culture as well as immortalizing selective PAECs, both for future use in various assays and screens and/or proteonomic profiles useful in generating a personalized pharmacotherapy regime, as disclosed herein.

Accordingly, it would be beneficial to provide systems and methods that provide solutions to this problem by utilizing PAECs obtained from a patient in order to measure the degree of a hyper-apoptotic and/or an anti-apoptotic phenotype within the respective PAEC cell population. Apoptosis is an active, ongoing process whereby cells induce self-destruction in response to cell-specific death signals specific due to the absence of cell survival signals. Under normal conditions the process is regulated by multiple factors so as to balance cell death with cell replacement. A cellular imbalance involving one or more of the factors may produce defects in apoptotic regulation, and in turn, create an imbalance between the two processes; a scenario often time associated with pathological conditions. It is known that altered or uncontrolled stimulation of endothelial cells is a common event associated with PAH. While the exact components and sequence of events controlling this process are not fully known, it is accepted that a progressive trait of PAH is associated with the emergence of proliferating apoptosis-resistant endothelial cells within the pulmonary artery region (see., e.g., Sakao et al., 2009, Respiratory Research 10:95-104). To this end, as a specific embodiment, but not meant to be limiting, dysfunctional PAECs are obtained from a patient diagnosed with PAH, whereby these cells are separated away from other cell types utilizing cell sorting methodology known in the art, followed by an appropriate PAEC-based screen or assay to determine the absence or presence (and degree) of an anti-apoptotic phenotype associated with the patient dysfunctional PAECs. Data generated from any such screen or assay will provide to the physician an additional disease state indicator allowing for diagnostic and prognostic indications leading to a personalized pharmacotherapy regime regarding future treatment of PAH. Thus, this embodiment of the present invention provides methods of determining the apoptotic state of a population of patient PAECs which comprises collecting cells from the region of the pulmonary artery, separating the PAECs away from the total recovered cell population, followed by cell culture of the separated PAECS and utilization in a cell-based screen or assay to determine the presence or absence of anti-apoptotic PAECs.

Numerous in vitro techniques are available to detect cellular apoptotic activity (or in contrast an anti-apoptotic proliferation phenotype) while differentiating from related but distinct processes of cell necrosis or other cell death activity. Preferred, but in no way limiting, techniques include any relevant in vitro cell-based assay utilizing the obtained, sorted PAECs, either recovered from passage through cell culture or via an immortalized cell line, to measure the presence of an apoptotic or anti-apoptotic cellular marker. Such assays include but are not limited to a caspase assay, a TUNEL and DNA fragmentation assay, cell permeability assays, an annexin V assay, a protein cleavage assay, or a mitochondrial ATP/ADP assay. The caspases consist of a group of aspartic acid-specific cysteine proteases which are activated during apoptosis and are synthesized as zymogens, become involved in apoptosis following proteolytic cleavage. Thus, caspase assays are based on the measurement of zymogen processing to an active enzyme and proteolytic activity. Multiple commercial kits are available to determine apoptotic activity based on caspase function. Such assays may measure caspase 8, caspase 9 or caspase 3/7, or alternatively may be an antibody based assay which detects a caspase 3 cleavage product. TUNEL and DNA fragmentation assays measure nuclease activity seen during apoptosis to generate DNA into small (about 180-200 base pairs in length). Again, multiple commercial assays are available to measure DNA fragmentation. Annexin V is a highly conserved 35 kDa protein that forms the voltage-dependent $Ca^{(2+)}$ channels in phospholipid bilayers. This calcium-dependent protein binds to phosphatidylserine which is normally situated on the inner surface of the cytoplasmic membrane. During apoptosis, phosphatidylserine is translocated to the outer surface, thus enabling it to be detected indirectly by annexin V staining, leading to multiple apoptosis assays. Additionally, in vitro cell toxicity and/or cell viability assays, also well known in the art, may be utilized to measure the apoptotic state of the recovered PAECs. It may be advantageous, and is within the scope of the present invention, to utilize multiple assays to best precisely identify an anti-apoptotic phenotype within the population of recovered PEACs.

In tissues such as skin and intestine, which are turned-over continually during the life of an organism, the cells forming these tissues undergo programmed cell death throughout the life of the organism. Various disease states occur due to aberrant regulation of programmed cell death in an organism. For example, defects that result in a decreased level of apoptosis in a tissue as compared to the normal level required to maintain the steady-state of the tissue can result in an increased number of cells in the tissue. Such a mechanism of increasing cell numbers has been identified in various cancers, where the formation of a tumor occurs not because the cancer cells necessarily are dividing more rapidly than their normal counterparts, bur because the cells are not dying at their normal rate. The first gene identified as being involved in a cell death pathway, the bcl-2 gene, was identified in cancer cells and was shown to function by decreasing the likelihood that cells expressing the gene would undergo apoptosis. In comparison to cancer, where the likelihood of a cell undergoing apoptosis is decreased, various pathologies are associated with tissues containing cells undergoing a higher than normal amount of apoptosis. For example, increased levels of apoptosis are observed in various neuropathologies, including Parkinson's disease, Alzheimer's disease, Huntington's disease and the encephalopathy associated with acquired immunodeficiency disease (AIDS). Since nerve cells generally do not divide in adults and, therefore, new cells are not available to replace the dying cells, the new cell death occurring in such diseases results in the progressively deteriorating condition of patients suffering from the disease.

Pulmonary arterial hypertension is normally confined to abnormalities within the pulmonary arterial blood vessels (i.e., "pre-capillary PH"), with the patient's hemodynamic profile indicating normal pulmonary venous pressure. As discussed herein, seminal diagnosis of PAH continues to rely on invasive right heart catheterization, also referred to as pulmonary artery catheterization (PAC). The disclosed embodiments are partially exemplified by utilization of a Swan-Ganz catheter, which is introduced into a central or peripheral vein (often a femoral vein, an internal jugular vein or a subclavian vein). From this entry site it is advanced (often with the aid of fluoroscopy) through the right atrium and wedged in a branch of the pulmonary artery in order to obtain a pressure reading within the right atrium, right ventricle, pulmonary artery, and the filling pressure of the left atrium. Utilization of a Swan-Ganz catheter is exemplified herein as both a method to determine the presence and severity of PAH, but more importantly as related to the present invention, as an instrument to recover and obtain a representative sample of the patient's total cell population within the pulmonary vasculature (which serves as the source from which a subpopulation of the patient's PAECs are recovered). The standard pulmonary artery catheter (such as the Swan-Ganz catheter) has two lumens and is equipped with an inflatable balloon at the tip, facilitating placement of the catheter into the pulmonary artery through the flow of blood. Inflation of the balloon portion of the catheter causes the catheter to wedge in a small pulmonary blood vessel, allowing for measurement of the relevant pressure readings and, as central to the ability to practice the present invention, recovery of a representative population of cells within the patient's pulmonary artery region which adhere to the inflated catheter during the procedure and which remain adhered to the catheter upon removal from the patient. As disclosed herein, a Swan Ganz catheter was utilized to carry out this step of the process of isolating a patient's PAECs (i.e., recovering the catheter upon removal from the patient, followed by washing of the catheter with and appropriate solution to retrieve a sample population of cells from the pulmonary artery region of the patient, representing the source from which PAECs are sorted from this total cell population and recovered in substantially pure form). However, it is evident that clinically acceptable variations of the exemplification disclosed herein are available to the clinician in regard to any catheter system or route of venous entry which may be utilized to practice this portion of the invention, namely recovery of a sample total cell population (of which a subset comprises the patient's PAECs), so long as inflation of the catheter system results in adherence of the patient's cells at the point of contact and this total cell population is amenable to recovery upon removal from the patient.

The PAECs may be substantially purified away from the total cell population by any and all means of cell sorting known in the art, including but not limited to various flow cytometry techniques, magnetic-based cell separation techniques available in the art, such as column-based technology (e.g., including but in no way limited to a MACS®-based separation technology) or tube-based methods (e.g., including but in no way limited to a Pro5®-based cell separation technology). One such well known methodology of cells sorting is Fluorescence Activated Cell Sorting (FACS), where the total population of cells is placed into a flask and the cells are forced into a small nozzle one at a time. The cells travel down the nozzle which is vibrated at an optimal frequency to produce drops at fixed distance from the nozzle. A subpopulation of cells (such as a patient's PAECs) may be identified and separated away from the total cell population by tagging cells of interest with a cell-specific antibody linked to a fluorescent dye. The antibody is bound to a protein that is uniquely expressed in the cells. The tagged cells are detected by light excitation of the dye, emitting a color of light that is detected by a photomultiplier tube, or light detector. By collecting the information from the light (scatter and fluorescence) a computer determines separation of the patient's PAECs away from the total cell population. The final step of sorting PAECs is accomplished by electrical charge. The computer determines how the cells will be sorted before the drop forms at the end of the stream. As the drop forms, an electrical charge is applied to the stream and the newly formed drop will form with a charge.

This charged drop is then deflected left or right by charged electrodes and into waiting sample tubes. Drops that contain no cells are sent into the waste tube. The end result is a pure subpopulation of the patient's PAEC cells, which may then be subjected to expansion via well know cell culture techniques. While FACS-based sorting is the preferred mode of cell sorting, other techniques are readily available and are represent additional methodology to obtain substantially pure patient PAECs, including but in now way limited to mechanical sorting of cell populations and fluidic switching sorters.

Catheters from 17 separate procedures were recovered, with optimal methodology, as described herein, resulting in obtaining between 200 to 4000 PAECs (CD45 negative) from the catheter, along with approximately 262,000 CD45 positive leukocytes. This corresponds with (based on ~1,600,000 C045 positive cells/mL of blood) approximately 170 uL of whole peripheral blood. The number of PAECs obtained appears to correlate to the recorded pressure (approximately 300 PAECs between 0-40 mm Hg; approximately 2250 PAECs between 41-90 mm Hg and approximately 3950 PAECs at a pressure of greater than 90 mm Hg). The PAECs obtained from patients diagnosed with either PAH or PH with left heart disease (i.e., left sided atrial or ventricular heart disease or left-sided valvular heart disease) by the disclosed methodology express, CD31 [(PECAM-1), associated with endothelial cells, monocytes, platelets, granulocytes, and B cells] CD146 [(S-Endo 1, MCAM or MUC18), associated with endothelial cells, melanomas and pericytes, and used herein as a marker for endothelial cell lineage]; CD105 [(Endoglin), associated with endothelial cells, bone marrow cell subset, and in vitro activated macrophages.]; and a subpopulation are CD133 [(PROM1), associated with endothelial progenitor cells, hematopoietic stem cells, and glioblastomas, with CD133 used herein as a marker for endothelial progenitor cells)]. Additionally, these PAECs are CD45 negative (a marker for leukocytes). As noted herein, respective PAEC subpopulations have been substantially isolated from patients diagnosed with either PAH or PH associated with left heart disease (i.e., left sided atrial or ventricular heart disease or left-sided valvular heart disease). These isolated PAECs have been serially passaged in cell culture, with PAECs isolated from PAH patients appearing to grow faster and to be more resistant to various forms of apoptotic stress compared to their (i) other PH PAEC counterparts isolated via the same technique, and (ii) commercially available vascular endothelial cells. Additionally, PAECs derived from PAH patients display sensitivities to compounds that do not have adverse effects on normal endothelial cells, and the reverse—abnormal PAECs resist some insults that kill normal endothelial cells.

As noted herein, this document further discloses PAECs obtained from individual patients by the methods disclosed herein, including but not limited to PAECs subjected to removal from the individual patient and a relevant cell sorting technique to provide for a substantially pure collection of the patient's PAECs, an isolated PAEC population provided through known cell subculture techniques, any isolated patient-derived PAEC cell line available in any useful form, such as but not including a cryopreserved PAEC cell line, and a PAEC-derived cell line which is an immortalized or transformed cell line, especially relating to an immortalized or transformed PAEC-derived cell line which exhibits a cellular phenotype of interest as related to generating a personalized pharmacotherapy regime as disclosed herein.

One of the major challenges in establishing a therapeutic regime to treat various forms of PH is that patients tend to respond differently to presently available first-line therapies, especially endothelial receptor antagonists (ERAs) and phosphodiesterase-5 inhibitors (PDE5s). And it is presently impossible to predict which class of drugs will be most effective in a newly diagnosed PH patient, including but not limited to a PAH patient. Regarding treatment of PAH, current therapeutic interventions target one of three pathways associated with pulmonary arterial endothelial and smooth muscle cells: endothelin-1, nitric oxide and prostacyclin. It will be accepted that PAEC dysfunction is a hallmark of PAH pathobiology. Such dysfunctional PAECs are associated with increased production of thromboxane A2 (a vasoconstrictor), a decrease in the production of nitric oxide and prostacyclin, and uncontrolled cell proliferation. Therefore, a challenge is to treat PH/PAH disorders with a drug, drug class or combination thereof which may promote a more normalized microvasculature setting within pulmonary arterial branches. One embodiment of the present invention disclosed use of a patient's recovered, sorted and cultured PAECs in one or multiple in vitro screens or assays to measure the phenotypic characteristics indicative of the stage of PH and/or to measure the cellular response to one or more drugs available to the clinician to treat a the specific form of PH. Results from such in vitro assays or screens measuring the effect of PH drugs on the individual patient's PAECs will allow the clinician to generate a personalized pharmacotherapeutic strategy to either initially select a drug of choice for patient administration or, in the alternative, to modify the present drug treatment regime based on the read-out of these assays or screens. The results from such assays or screens may suggest a stand-alone therapy or possibly may point to a combination therapy as the most prudent prognostic indication. To this end, the disclosed embodiments further relate to methods of obtaining PAECs directly from the pulmonary vasculature of living patients which comprises retrieving these cells from the individual patient, substantially purifying the PAECs away from the total cell population, amplifying the PAECs in cell culture and utilizing these substantially purified PAECs (whether as primary in vitro cultured cells, secondary in vitro cultured cells, or as an immortalized cell line) in one or multiple in vitro cell-based assays or screens to generate a patient-specific pharmacologic profile concerning the respective PH-based disorder to assist the clinician in generating a treatment regime tailored to the individual patient.

The disclosed embodiments further relate to methods of analyzing one or a combination of biomarkers obtained from cultured patient PAECs to individualize treatment of PH disorders, including but not limited to PAH. In some instances, the isolated PAECs can be stimulated in vitro with one or more growth factors before, during, and/or after incubation with one or more compounds of interest. Additionally, the isolated PAECs may be lysed following treatment to produce a cellular extract by any technique known in the art. To this end, the isolated PAECs may be utilized to generate a protein profile comprising a protein expression profile, protein activation profile, and combinations thereof, including but not limited to full-proteonome profiling with 2-D gels or multi-dimensional chromatography, such as disclosed in Geguchadze et al., (2012) J. Dent. Res. 91 (4):382-386, which is incorporated in its entirety. Such a protein expression profile comprises determining the expression level of at least one protein selected from the group consisting of endothelin-1, phosphodiesterase-5, prostacyclin, cGMP (as well as any measurable intracellular components and/or signals associated with endothelin-1, phosphodiesterase-5, prostacyclin, and cGMP), Caveolin-1, STAT3, NFAT, Bcl-2, BMPR-II, p53, p21, myc, ras, ALDH, CD34 (L-selectin), Von Willebrand factor (vWF), CD117 (c-Kit), CD309 (VEGFR-2), CD48, CD144 (VE-cadherin), CD31 (PECAM-1), CD146 (S-Endo, MCAM or MUC18), CD 105 (Endoglin), and CD133 (PROM1). Additionally, procedures well known in the art may be utilized to generate full-proteonome profiles for various diagnostic strategies as disclosed herein, which may in some combination identify one or more biomarkers or potential drug screening tools recited in within this paragraph and/or disclosure.

A myriad of techniques are available to the artisan to detect the presence of a protein and/or the level of expression of the protein(s) of interest within the isolated PAECs. Oftentimes the presence or level of the proteinaceous biomarker is determined using antibodies specific for the biomarker and detecting specific binding. Such techniques include but are not limited to an immunoassay, which may be competitive or non-competitive in nature, includes but is not limited to enzyme immunoassays (EIA) such as enzyme multiplied immunoassay technique (EMIT), enzyme-linked immunosorbent assay (ELISA), IgM antibody capture ELISA (MAC ELISA), microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). Specific immunological binding of the antibody to the proteinaceous biomarker can be detected directly or indirectly. Direct labels include fluorescent or luminescent tags, metals, dyes, radionuclides, and the like, attached to the antibody. A chemiluminescence assay using a chemiluminescent antibody specific for the biomarker is suitable for sensitive, non-radioactive detection of biomarker levels. An antibody labeled with fluorochrome is also suitable for determining the level of one or more biomarkers in a sample. And as known in the art, signal detection will depend upon the type of direct or indirect label used in that particular assay. Specifically, an antigen capture assay is contemplated for use in practicing certain embodiments of the present invention. For example, in an antigen capture assay, an antibody directed to a proteinaceous biomarker of interest is bound to a solid phase and sample is added such that the biomarker is bound by the antibody. After unbound proteins are removed by washing, the amount of bound marker can be quantitated using, for example, a radioimmunoassay. Sandwich enzyme immunoassays can also be useful in the methods of the present invention. For example, in a two-antibody sandwich assay, a first antibody is bound to a solid support, and the biomarker is allowed to bind to the first antibody. The amount of the biomarker is quantitated by measuring the amount of a second antibody that binds the biomarker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot. Quantitative Western blotting also can be used to detect or determine the level of one or more proteinaceous biomarkers in a sample. Western blots can be quantitated by well-known methods such as scanning densitometry or phosphorimaging. In certain instances, methods well known in the art include autoradiographs of the blots being analyzed using a scanning densitometer and normalized to a positive control. Alternatively, a variety of immunohistochemistry (IHC) techniques can be used to determine the level of one or more proteinaceous biomarkers in a sample. An IHC technique encompasses techniques that utilize the visual detection of fluorescent dyes or enzymes coupled (i.e., conjugated) to antibodies that react with the biomarker using fluorescent microscopy or light microscopy and includes, without limitation, direct fluorescent antibody, indirect fluorescent antibody (IFA), anticomplement immunofluorescence, avidin-biotin immunofluorescence, and immunoperoxidase assays. An IFA assay, for example, is useful for determining whether a sample is positive for a particular marker of interest, the level of that marker, and/or the staining pattern of that marker. The concentration of the marker in a sample can be quantitated, e.g., through endpoint titration or through measuring the visual intensity of fluorescence compared to a known reference standard. The presence or level of a proteinaceous biomarker can also be determined by detecting or quantifying the amount of the purified marker. Purification of the marker can be achieved, for example, by high pressure liquid chromatography (HPLC), alone or in combination with mass spectrometry (e.g., MALDI/MS, MALDI-TOF/MS, tandem MS, etc.). Qualitative or quantitative detection of a biomarker can also be determined by well-known methods including, without limitation, Bradford assays, Coomassie blue staining, silver staining, assays for radiolabeled protein, and mass spectrometry. The analysis of a plurality of proteinaceous biomarkers may be carried out separately or simultaneously with one test sample. Particularly useful physical formats comprise surfaces having a plurality of discrete, addressable locations for the detection of a plurality of different biomarkers. Such formats include protein microarrays, or protein chips and certain capillary devices. In these embodiments, each discrete surface location may comprise antibodies to immobilize one or more biomarkers for detection at each location. Surfaces may alternatively comprise one or more discrete particles (e.g., microparticles or nanoparticles) immobilized at discrete locations of a surface, where the microparticles comprise antibodies to immobilize one or more biomarkers for detection. Analysis of the activation or inhibition of proteinaceous biomarkers of interest can be used alone or in combination with other markers to predict, monitor, or optimize tyrosine kinase inhibitor therapy in a subject according to the methods of the present invention. Any method known in the art for detecting or determining the activity or activation state of one or more of the biomarkers described herein is suitable for use in the present invention. In some embodiments, the activation or inhibition of a proteinaceous biomarker can be determined by molecular cytogenetic techniques such as immunocytochemistry or immunohistochemistry (IHC). An IHC assay is particularly useful for determining the phosphorylation state of proteins that are activated or inhibited by phosphorylation at specific tyrosine, serine, and/or threonine residues. In particular, IHC can be performed to determine whether a sample is positive for a particular phosphorylated marker of interest, the level of that phosphorylated marker, and/or the staining pattern of that phosphorylated marker. Other methods for detecting the phosphorylation state of a protein of interest include, but are not limited to, KIRA ELISA, mass spectrometry and eTag™ assay system. In view of the above, one skilled in the art will readily appreciate that the methods for determining a protein expression profile or a protein activation profile from isolated PAECs can be practiced using one or any combination of the well-known techniques described above or other techniques known in the art. When at least one of the proteinaceous biomarkers of interest is an enzyme, a level of enzymatic activity can be determined to assess the activation state of the enzyme. In some embodiments, the activation state of interest corresponds to the phosphorylation state of a proteinaceous biomarker, the ubiquitination state of the biomarker, or the complexation state of the biomarker with another cellular molecule (e.g., VEGFR-2). Any method now or hereafter known in the art can be used to detect the complexation state of a proteinaceous biomarker of interest with another cellular molecule. Preferably, the formation of heterodimeric complexes between members of the EGFR family of receptor tyrosine kinases are detected in tumors or tumor cells. Several methods are described below. These methods generally detect noncovalent protein-protein interactions between proteins of interest. Additionally, Immuno-affinity-based methods, such as immunoprecipitation or ELISA, can be used to detect heterodimeric complexes between proteins of interest (e.g., VEGFR-2 heterodimers).

Any in vitro cell-based screen now or hereafter known in the art may be utilized by the artisan to screen for a compound which interacts with a target molecule on a respective in vitro PAEC culture. As a non-limiting example, endothelin-1 is a biologically active peptide that can produce a change in a human or animal when it interacts with an endogenous macromolecular receptor molecule such as an endothelin receptor (e.g., $ET_A$ or $ET_B$). An endothelin agonist is a drug that increases a physiological activity and/or biochemical function of the endothelin receptor when the drug is bound to or forms a complex with the receptor. An endothelin antagonist is a drug or biologically active molecule that reduces or removes or partially or totally inhibits a physiological activity and/or biochemical function of the receptor when the antagonist is bound to or forms a complex with the endothelin receptor. The biological function or process in which the receptor participates can have an excitatory or an inhibitory mechanism. Each endothelin agonist and each endothelin antagonist drug would a relative affinity for the endothelin receptor molecule to which it binds to form a drug-receptor complex. The relative affinity of an agonist drug or of an antagonist drug can be represented by an equilibrium association constant or equilibrium dissociation constant for the drug-receptor complex. An agonist and an antagonist can bind to substantially similar sites on a receptor molecule or to different sites on a receptor. The binding affinity between a drug and a receptor molecule can depend on a number of parameters including the molecular structure of the drug, the number of rotational degrees of freedom of the drug molecule, the presence of charged or polarized functional groups in the drug molecule, the present of functional groups having the ability to form hydrogen bonds with the receptor molecule and with other molecules proximal to the receptor binding site, the conformational flexibility of the drug molecule, the ability of a drug to form van der Waals interactions with functional groups in a receptor which can be the result of favorable molecular orbital overlap between drug and receptor molecular orbitals of similar energy that leads to a net lowering of energy levels and increased binding, the kind and number of substituents in a drug molecule, and the relative spacial or stereospecific orientation of the functional groups in the drug that interact with functional groups in the receptor molecule. In a group of molecules that exhibit antagonist activity for an endothelin receptor, different antagonist molecules can bind to substantially the same site on the receptor molecule as other antagonists or to different sites on the receptor molecule, or to both the same and different sites on the endothelin receptor. An antagonist may remove either an excitatory or inhibitory mechanism controlling bodily processes. In vitro screening assays have been used to identify active compounds that exhibit agonist or antagonist activity as ligands that bind to a receptor such as a protein, antibody, or enzyme that can be present at the surface or inside of a cell or that can be isolated from a cell or tissue or blood of an animal or that can be prepared by recombinant methods. Cells containing receptors used in screening assays can sometimes be grown in culture media or isolated from living or dead tissue, and a receptor useful in an assay can be isolated from such cells. In a receptor-ligand binding assay, active compounds that are found to exhibit a desired level of binding affinity to a receptor can be hit compounds or lead compounds. By "hit compounds" is meant the compounds exhibiting binding affinity and are $ET_A$-receptor selective, $ET_B$ selective or non selective for $ET_A$ and $ET_B$. By "lead compounds" is meant the compound exhibiting binding affinity to ETA receptor selective. Such compounds can be useful as pharmaceutical or therapeutic agents or as leads in the discovery of pharmaceutical or therapeutic agents. For an antagonist identified by a screening process, a dose-response relationship between the antagonist and a receptor can be determined relative to the dose-response of a standard or reference antagonist compound. Thereafter, structural analogs of the antagonist can be prepared and the dose-response relationships of these compounds can be used to define the pharmacophore or region of molecular stereospecific binding activity between the antagonist and the receptor. In a drug discovery process, random screening assays that subject an aliquot of a sample containing naturally occurring or synthetic compounds or a mixture of such compounds to a screening procedure have been used to identify the presence of one or more active compounds in the aliquot. Active compounds are considered to be those compounds that exhibit a predetermined or better than predetermined level of activity in an in vitro biological assay system. To increase the probability of finding an active antagonist compound from a screening assay, a large number of compounds or mixtures of compounds are often examined. These compounds are often diverse in structure and origin and can be expensive and time-consuming to screen and analyze. It is therefore desirable to be able to reduce the number of compounds examined and shorten the time required to find compounds that exhibit antagonist activity against a receptor. The source of a compound or a mixture of compounds typically subjected to a screening assay is frequently a library of compounds that have been prepared by synthetic chemical processes and/or from randomly selected natural product sources such as isolates from plant and animal sources. It is frequently desired that a library of compounds used for random screening be as diverse as possible and contain compounds from a variety of different sources to optimize the changes of finding an active compound in a screening assay. In certain screening assays, radioisotopic labeling of reference compounds used as reagents in competitive binding assays has been employed. However, radionuclide-labeled compounds for these assays can be expensive, unstable, and time consuming to prepare, and the specific radioactivity decays with time as a function of the isotope used. Radionuclides always require isolation of the work environment where an assay is performed, and often require dedication of apparatus for their preparation, handling, and analysis. Monitoring of human exposure and health risks is required; waste disposal and transportation is regulated and can be complicated; and substantial technical training and documentation is mandatory. In other screening assays, fluorescent-labeled antibodies have been used in immunoassays. However, these too can be expensive, and can be sensitive to denaturing during handling. Thus, a screening procedure that obviates the need for radionuclide labeling and handling or eliminates the need for antibodies will be useful. Thus, dysfunctional PAECs subjected to the in vitro assays and screens as well as proteonomic profiling may reveal specific biomarkers which will serve as a tool, indicator, target or such in the artisan's particular drug screening procedure.

Examples

Catheters from 17 separate procedures were recovered, with optimal methodology, as described herein, resulting in obtaining between 200 to 4000 PAECs (CD45 negative) from the catheter, along with approximately 262,000 CD45 positive leukocytes. This corresponds with (based on ~1,600,000 C045 positive cells/mL of blood) approximately 170 uL of whole peripheral blood. The number of PAECs obtained appears to correlate to the recorded pressure (approximately 300 PAECs between 0-40 mm Hg; approximately 2250 PAECs between 41-90 mm Hg and approximately 3950 PAECs at a pressure of greater than 90 mm Hg). The PAECs obtained from patients diagnosed with either PAH or PH with left heart disease (i.e., left sided atrial or ventricular heart disease or left-sided valvular heart disease) by the disclosed methodology express, CD31 [(PECAM-1), associated with endothelial cells, monocytes, platelets, granulocytes, and B cells] CD146 [(S-Endo 1, MCAM or MUC18), associated with endothelial cells, melanomas and pericytes, and used herein as a marker for endothelial cell lineage]; CD105 [(Endoglin), associated with endothelial cells, bone marrow cell subset, and in vitro activated macrophages.]; and a subpopulation are CD133 [(PROM1), associated with endothelial progenitor cells, hematopoietic stem cells, and glioblastomas, with CD133 used herein as a marker for endothelial progenitor cells)]. Additionally, these PAECs are CD45 negative (a marker for leukocytes). As noted herein, respective PAEC subpopulations have been substantially isolated from patients diagnosed with either PAH or PH associated with left heart disease (i.e., left sided atrial or ventricular heart disease or left-sided valvular heart disease). These isolated PAECs have been serially passaged in cell culture, with PAECs isolated from PAH patients appearing to grow faster and to be more resistant to various forms of apoptotic stress compared to their (i) other PH PAEC counterparts isolated via the same technique, and (ii) commercially available vascular endothelial cells. Additionally, PAECs derived from PAH patients display sensitivities to compounds that do not have adverse effects on normal endothelial cells, and the reverse—abnormal PAECs resist some insults that kill normal endothelial cells.

Cell Isolation. The last two inches of the catheter is cut and placed in a tube containing endothelial cell media and placed on ice till the samples can be further processed. All subsequent steps are performed on ice or at 4° C. To process the samples the catheter tips are removed from the tube containing the media and placed in a tube containing 1×PBS, and trypsin. The catheter is subsequently washed with this solution and then placed in a third tube. The three tubes are then spun down at 1,500 rpm for 10 minutes. The resulting pellets are then re-suspended and combined in an ACK/PBS solution to lyse the red blood cells. The resulting suspension is transferred to a 1.5 mL tube and centrifuged at 2,500 rpm for 10 minutes to pellet the cells. The resulting cells are then re-suspended in FACS Buffer (PBS, 10% FBS), and then stained with antibodies for CD146 (PE-conjugated), CD45 (APC-conjugated) and CD31 (FITC-conjugated) and sorted by FACS analysis and the CD31+, CD146+ and CD45- fraction is collected for future culture and analysis.

Cell Culture. The resulting cells are plated on tissue culture plates coated with Endothelial Cell Attachment Factor (ECAF), and are grown in Endothelial Cell Growth Medium (Cell Applications Inc.). The day after plating, the cells are washed with 1×PBS and fresh growth media is added to the cells. The cells are split when the plate is either 75% confluent or when "colonies" become too large.

Figure 2:
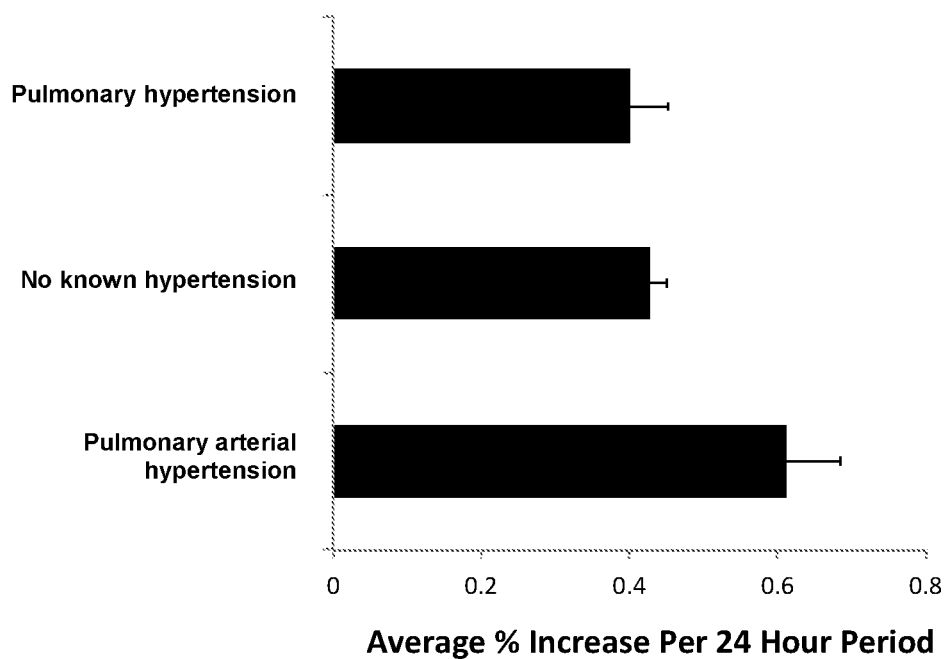
FIG. 2 shows Western blot analysis of Bcl-2 (B-cell lymphoma 2) protein concentrations in PAECs from PAH patients.

Pulmonary arterial endothelial cells were isolated from three groups of patients; 1) with pulmonary arterial hypertension, 2) with pulmonary hypertension, and 3) a patient population without hypertension using the techniques described herein. Cell culture experiments, in which cells were counted at incremental periods, showed growth kinetics in the PAH group were approximately 50% greater than those observed with the other two groups (FIG. 1). Further analyses of these cells showed via Western Blots showed Bcl-2 (B-cell lymphoma 2) protein concentrations in PAECs from PAH patients to be in excess of 70% greater than those in the other experimental groups (FIG. 2).

The invention claimed is:

1. A method of culturing a population of pulmonary arterial endothelial cells from a patient, comprising:
   introducing an inflatable balloon catheter into a vein of the patient and advancing the catheter through the right heart of the patient and into a branch of the pulmonary artery of the patient;
   inflating the balloon catheter to a pressure consistent with that of a pulmonary artery catheter;
   removing the balloon catheter from the patient;
   collecting a total cell population that adheres to the balloon catheter after removal from the patient;
   purifying the population of pulmonary endothelial cells away from the total cell population; and
   expanding the population of pulmonary endothelial cells in a growth medium.

2. The method of claim 1, wherein the patient shows symptoms of or is diagnosed with pulmonary hypertension.

3. The method of claim 2, wherein the patient shows symptoms of or is diagnosed with a form of pulmonary hypertension selected from the group consisting of pulmonary arterial hypertension, left-sided atrial heart disease, left-sided ventricular heart disease, pulmonary hypertension associated with lung diseases and/or hypoxemia, pulmonary hypertension due to chronic thrombotic and/or embolic disease, sarcoidosis, histiocytosis X, lymphangiomatosis, adenopathy associated with compression of pulmonary vessels, tumor presence associated with compression of pulmonary vessels, and fibrosing mediastinitis associated with compression of pulmonary vessels.

4. The method of claim 1, wherein the pulmonary arterial endothelial cells express CD31, CD146, CD105 and/or CD133, and/or are CD45 negative.

5. The method of claim 1, further comprising passaging of the pulmonary arterial endothelial cells in culture.

6. The method of claim 1, wherein performing the cell purification process comprises using flow cytometry, magnetic-based cell separation, or fluorescence activated cell sorting to separate the pulmonary arterial endothelial cells away from the total cell population.

7. The method of claim 1, further comprising performing one or more in vitro cell-based screens or assays on the pulmonary arterial endothelial cells to measure one or a combination of biomarkers associated with a pulmonary hypertension disorder.

8. The method of claim 7, further comprising:
based on the one or more in vitro cell-based screens or assays, selecting and providing to the patient a personalized pharmacotherapy regime for the patient concerning the treatment of a pulmonary hypertension disorder.

9. The method of claim 8, wherein the in vitro cell-based screen or assay comprises measurement of Bcl-2 or BMPR-II expression.

10. The method of claim 1, further comprising performing one or more in vitro cell-based screens or assays to measure:
cellular phenotypic characteristics indicative of a stage of pulmonary hypertension in the population of pulmonary arterial endothelial cells; or
cellular phenotypic characteristics indicative of detectable transformation of at least a threshold percentage of the population of pulmonary arterial endothelial cells from a normal cellular apoptotic state to a hyper-apoptotic state or an anti-apoptotic state.

11. The method of claim 10, wherein:
a determination that at least a threshold percentage of the population of pulmonary arterial endothelial cells are in a hyper-apoptotic state indicates that the patient exhibits an early stage of pulmonary vascular disease; and
a determination that at least a threshold percentage of the population of pulmonary arterial endothelial cells are in an anti-apoptotic state indicates that the patient exhibits a late stage of pulmonary vascular disease.

12. A method of culturing a population of pulmonary arterial endothelial cells from a patient, comprising:
introducing an inflatable balloon catheter into a vein of a patient who shows symptoms of or is diagnosed with pulmonary hypertension and advancing the catheter through the right heart of the patient and into a branch of the pulmonary artery of the patient;
inflating the balloon catheter to a pressure consistent with that of a pulmonary artery catheter;
removing the balloon catheter from the patient;
collecting a total cell population that adheres to the balloon catheter after removal from the patient;
using flow cytometry, magnetic-based cell separation, or fluorescence activated cell sorting to separate the pulmonary arterial endothelial cells away from the total cell population; and
expanding the population of pulmonary endothelial cells in a growth medium.

13. The method of claim 12, wherein the patient shows symptoms of or is diagnosed with a form of pulmonary hypertension selected from the group consisting of pulmonary arterial hypertension, left-sided atrial heart disease, left-sided ventricular heart disease, pulmonary hypertension associated with lung diseases and/or hypoxemia, pulmonary hypertension due to chronic thrombotic and/or embolic disease, sarcoidosis, histiocytosis X, lymphangiomatosis, adenopathy associated with compression of pulmonary vessels, tumor presence associated with compression of pulmonary vessels, and fibrosing mediastinitis associated with compression of pulmonary vessels.

14. The method of claim 12, wherein the pulmonary arterial endothelial cells express CD31, CD146, CD105 and/or CD133, and/or are CD45 negative.

15. The method of claim 12, further comprising passaging of the pulmonary arterial endothelial cells in culture.

16. The method of claim 12, further comprising performing one or more in vitro cell-based screens or assays on the pulmonary arterial endothelial cells to measure one or a combination of biomarkers associated with a pulmonary hypertension disorder.

17. The method of claim 16, further comprising:
based on the one or more in vitro cell-based screens or assays, selecting and providing to the patient a personalized pharmacotherapy regime for the patient concerning the treatment of a pulmonary hypertension disorder.

18. The method of claim 17, wherein the in vitro cell-based screen or assay comprises measurement of Bcl-2 or BMPR-II expression.

19. The method of claim 12, further comprising performing one or more in vitro cell-based screens or assays to measure:
cellular phenotypic characteristics indicative of a stage of pulmonary hypertension in the population of pulmonary arterial endothelial cells; or
cellular phenotypic characteristics indicative of detectable transformation of at least a threshold percentage of the population of pulmonary arterial endothelial cells from a normal cellular apoptotic state to a hyper-apoptotic state or an anti-apoptotic state.

20. The method of claim 12, further comprising performing one or more in vitro cell-based screens or assays to determine whether at least a threshold percentage of the population of pulmonary arterial endothelial cells has transformed from a normal cellular apoptotic state to a hyper-apoptotic state or an anti-apoptotic state, wherein:
a determination that at least a threshold percentage of the population of pulmonary arterial endothelial cells are in a hyper-apoptotic state indicates that the patient exhibits an early stage of pulmonary vascular disease; and
a determination that at least a threshold percentage of the population of pulmonary arterial endothelial cells are in an anti-apoptotic state indicates that the patient exhibits a late stage of pulmonary vascular disease.

\* \* \* \* \*